US012697225B2

(12) United States Patent
Baynham

(10) Patent No.: US 12,697,225 B2
(45) Date of Patent: Aug. 4, 2026

(54) EXPANDABLE CORPECTOMY DEVICE

(71) Applicant: ATLAS SPINE, INC., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 183 days.

(21) Appl. No.: 18/754,824

(22) Filed: Jun. 26, 2024

(65) Prior Publication Data

US 2026/0000518 A1     Jan. 1, 2026

(51) Int. Cl.
*A61F 2/44*          (2006.01)
*A61F 2/30*          (2006.01)

(52) U.S. Cl.
CPC ...... *A61F 2/44* (2013.01); *A61F 2002/30537* (2013.01); *A61F 2002/443* (2013.01)

(58) Field of Classification Search
CPC .......... A61F 2/44; A61F 2/447; A61F 2/4455; A61F 2002/30537; A61F 2002/443
See application file for complete search history.

(56) References Cited

U.S. PATENT DOCUMENTS

| | | | |
|---|---|---|---|
| 9,211,197 B2 | 12/2015 | Baynham | |
| 9,925,061 B2 | 3/2018 | Baynham | |
| 9,956,090 B2 | 5/2018 | Baynham | |
| 11,458,024 B2 * | 10/2022 | Berry | A61F 2/4425 |
| 2008/0281424 A1 * | 11/2008 | Parry | A61F 2/4611 |
| | | | 606/151 |

| | | | |
|---|---|---|---|
| 2009/0112320 A1 * | 4/2009 | Kraus | A61F 2/44 |
| | | | 606/90 |
| 2010/0280616 A1 * | 11/2010 | Frasier | A61F 2/4611 |
| | | | 623/17.16 |
| 2012/0179255 A1 * | 7/2012 | DeFalco | A61F 2/4611 |
| | | | 623/17.11 |
| 2012/0209384 A1 * | 8/2012 | Arnold | A61F 2/4465 |
| | | | 623/17.15 |
| 2014/0207236 A1 * | 7/2014 | Prevost | A61F 2/4425 |
| | | | 623/17.16 |
| 2014/0277470 A1 * | 9/2014 | Baynham | A61F 2/447 |
| | | | 623/17.13 |

(Continued)

FOREIGN PATENT DOCUMENTS

AU          2021201171 A1 *   3/2021   ............ A61F 2/4611

*Primary Examiner* — Eduardo C Robert
*Assistant Examiner* — Holly Joanna Lane
(74) *Attorney, Agent, or Firm* — McHale & Slavin, P.A.

(57)          ABSTRACT

The instant invention is a longitudinally adjustable corpectomy device which fits within the intervertebral distracted channel. The device employs a base member constructed to receive an expansion member, the base member having an engagement surface formed on a back wall. The base member further includes a rack formed along an outer surface of the lower section and a reciprocal engagement surface on a back wall. A gear member is rotatably secured to the base member to engage the rack of the expansion member wherein rotation of the gear member allows a raising or lowering of said expansion member. A lock fastener is operatively associated with the base member for use in coupling the reciprocal engagement surface to the engagement surface arresting movement of said expansion member in relation to the base member. An upper endplate is angularly adjustable.

14 Claims, 18 Drawing Sheets

(56)                    References Cited

U.S. PATENT DOCUMENTS

| 2014/0277480 A1* | 9/2014 | Prevost | ..................... | A61F 2/44 |
| | | | | 623/17.16 |
| 2015/0032210 A1* | 1/2015 | Stinchfield | ................ | A61F 2/44 |
| | | | | 623/17.16 |

* cited by examiner

SECTION I-I

SECTION II-II

EXPANDABLE CORPECTOMY DEVICE

FIELD OF THE INVENTION

The invention generally relates to improvements to vertebral implants and, more particularly, to a longitudinally expandable vertebral implant configured for incremental expansion by a gear driven expander for ease of securement at any desired increment in situ.

BACKGROUND OF THE INVENTION

The spine consists of vertebrae that are categorized into sections known as the cervical, thoracic and lumbar section in a flexible arranged column. The vertebrae are separated by small cartilaginous cushions known as intervertebral discs. Intervertebral discs are oblate structures that maintain the space between adjacent vertebrae. Each intervertebral disc consists of an outer annulus fibrosus, which surrounds the inner nucleus pulposus. The annulus fibrosus consists of several layers of strong annular fibrocartilage to contain the nucleus pulposus and distribute pressure evenly across the disc wherein a mucoprotein gel serves to absorb shocks.

Deterioration of an intervertebral disc results in limited mobility and can cause severe pain. For instance, normal aging causes the nucleus pulposus to lose fluid and contract in volume resulting in a reduction in the intervertebral space. Any reduction of space between adjacent vertebrae may put pressure on the nerves of the spinal column. Further, a reduction in volume of the nucleus pulposus reduces the disc's ability to absorb shock which can result in disc herniation. The bulge of a herniated disc may also put pressure on nearby nerve structures resulting in pain as well as diminished range of motion.

Surgical options are available including laminectomy and discectomy combined with vertebral fusion and/or dynamic stabilization. However, these surgical options are highly invasive and require prolonged hospitalization and recovery. More recently, artificial disc replacement prosthetics have been used to replace or augment all or part of the removed or resected intervertebral disc.

In order to reduce the pain associated with the movement of the intervertebral joint, surgical intervention is often indicated as a means to alleviate pressure upon the spinal cord while concomitantly stabilizing the associated vertebrae. This involves a surgical procedure to distract the disc and or vertebra, or portions thereof, and the insertion of bone fusing material into the cavity of the opposing vertebra. Corpectomy devices have been developed to help support the spine and maintain the normal spacing between opposing vertebrae. A corpectomy is a surgical procedure that involves the removal of a vertebral body and adjacent intervertebral discs to decompress the spinal cord or nerves, usually to relieve pressure caused by spinal cord compression. A corpectomy device is used to provide stability and support to the spine after the procedure, conventionally cages or spacers used to maintain spinal alignment and promote fusion of the remaining vertebrae. Some of these devices may be packed with fusing material to ensure solid bone growth between the two vertebrae.

U.S. Pat. Nos. 9,211,197 and 9,925,061 disclose longitudinally adjustable corpectomy devices. A ratchet mechanism allows for an extendable member to adjust to a longer length and a ratchet type mechanism allows member movement in a unidirectional pattern to prevent the members from contracting once expanded.

U.S. Pat. No. 9,956,090 discloses an adjustable corpectomy device having a main body, a first expandable plate, and an opposing second expandable plate. Each expandable plate is adapted to fit within the main body in a compressed state, and extends away from the main body in a non-compressed, expanded state.

SUMMARY OF THE INVENTION

The instant invention is a longitudinally adjustable corpectomy device which fits within the intervertebral distracted channel. The device employs a base member defined by four walls having a lower edge and an upper edge forming a cavity therebetween with an engagement surface formed along an inner surface of a rear wall. An expansion member having an upper section with an adjustable upper endplate and a lower section, the lower section is slidably insertable into the cavity of the base member and including a rack formed along an outer surface of said lower section and a reciprocal engagement surface on a back wall. A gear member rotatably secured to the base member to engage the rack of the expansion member wherein rotation of the gear member allows a raising or lowering of said expansion member. A press fastener is operatively associated with the base member for use in coupling the reciprocal engagement surface to the engagement surface.

An objective of the instant invention to provide a corpectomy device that may be adjusted within the intervertebral cavity or adjusted in situ within the cavity.

It is a further objective of the instant invention to provide an expandable corpectomy wherein rotation of a gear member adjusts the height of an expansion member in relation to a base member, and a press fastener locks the expansion member to the base member.

Still another objective of the invention is to teach the use of an engagement member having a reciprocal member that can be locked together by a press fastener to arrest expansion movement.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
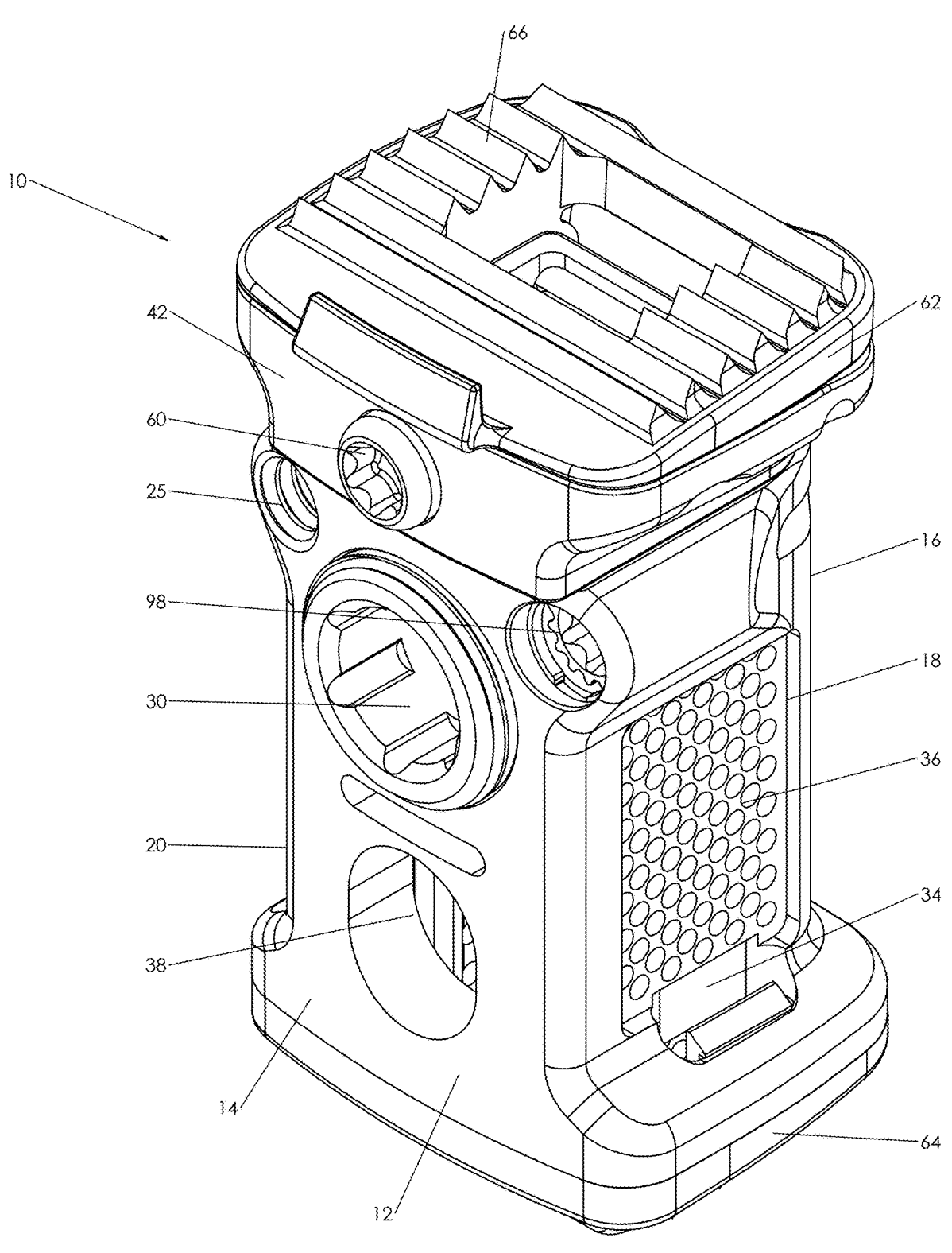
FIG. 1 is a top front perspective view of the corpectomy device in a compressed position.
Figure 2:
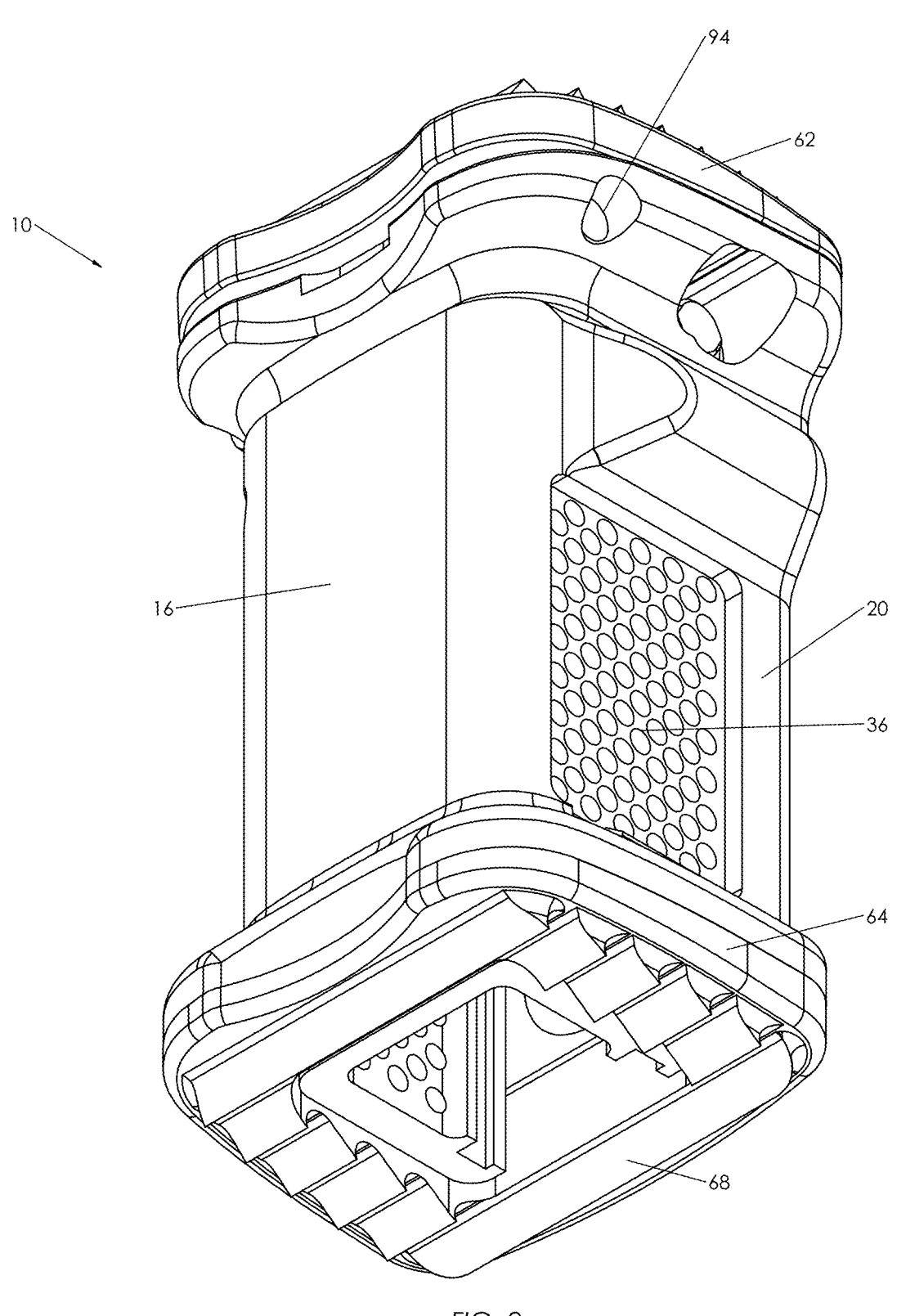
FIG. 2 is a bottom rear perspective view thereof.
Figure 3:
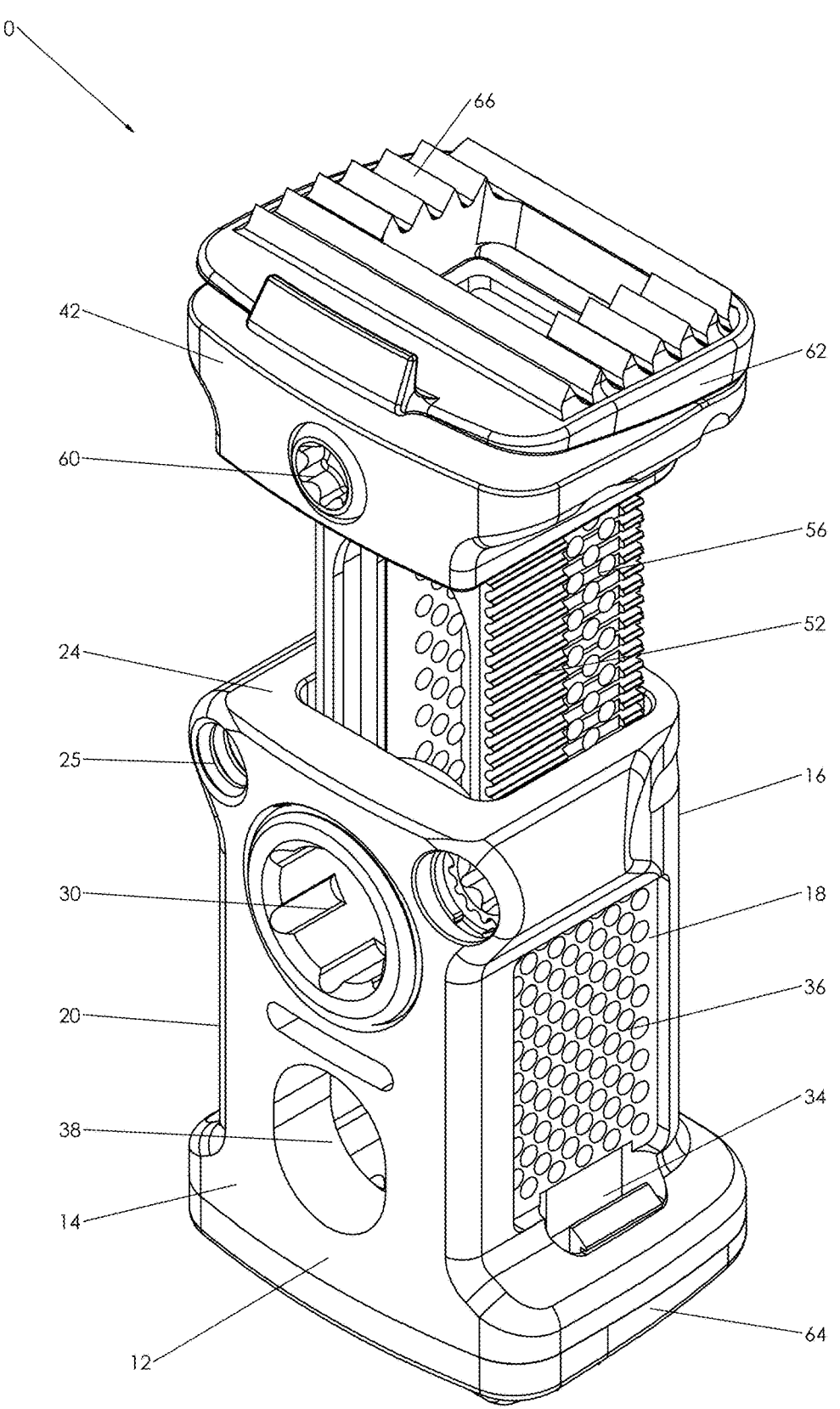
FIG. 3 is a top front perspective view in an expanded position.
Figure 4:
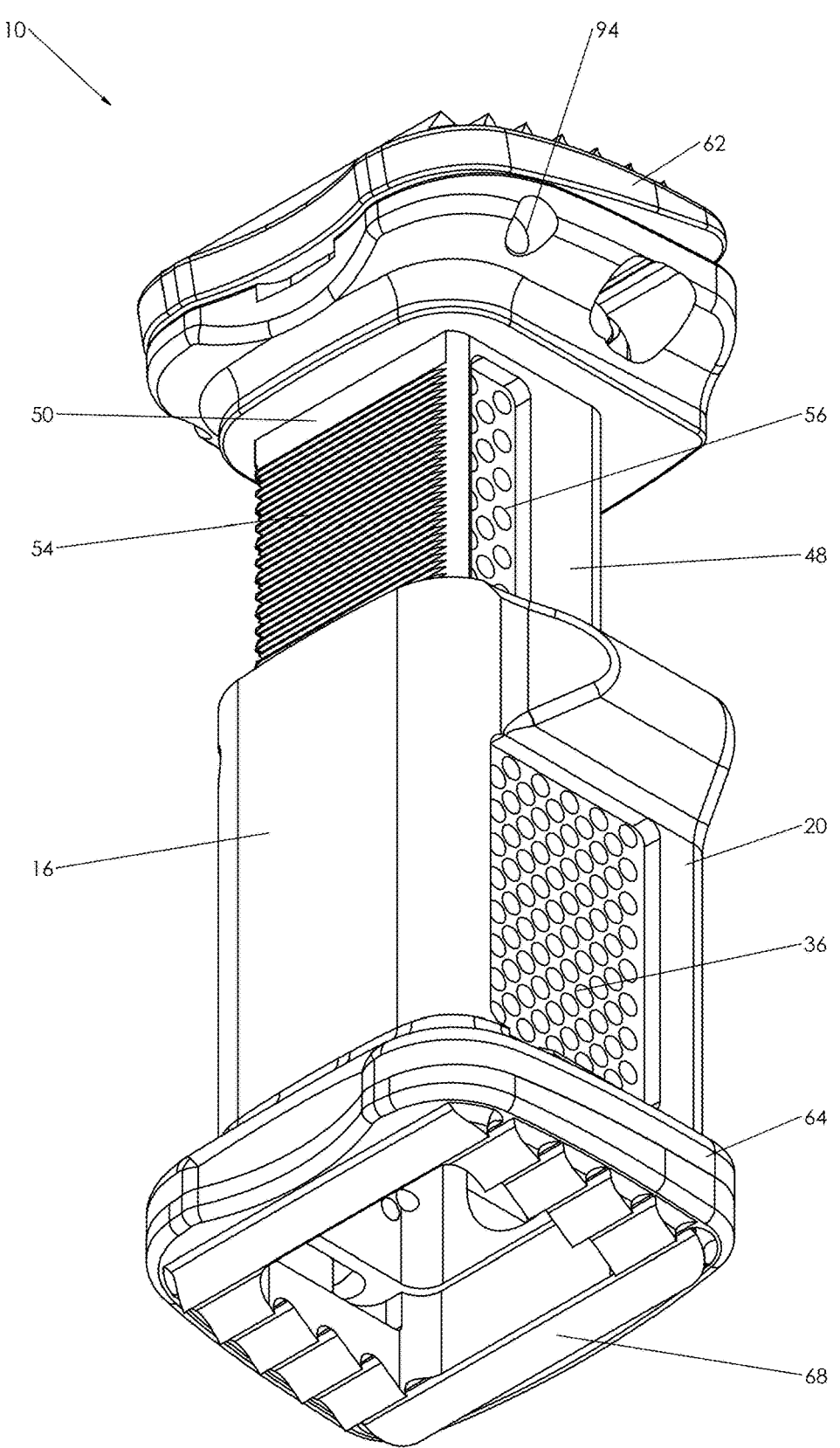
FIG. 4 is a bottom rear perspective view in an expanded position.
Figure 5:
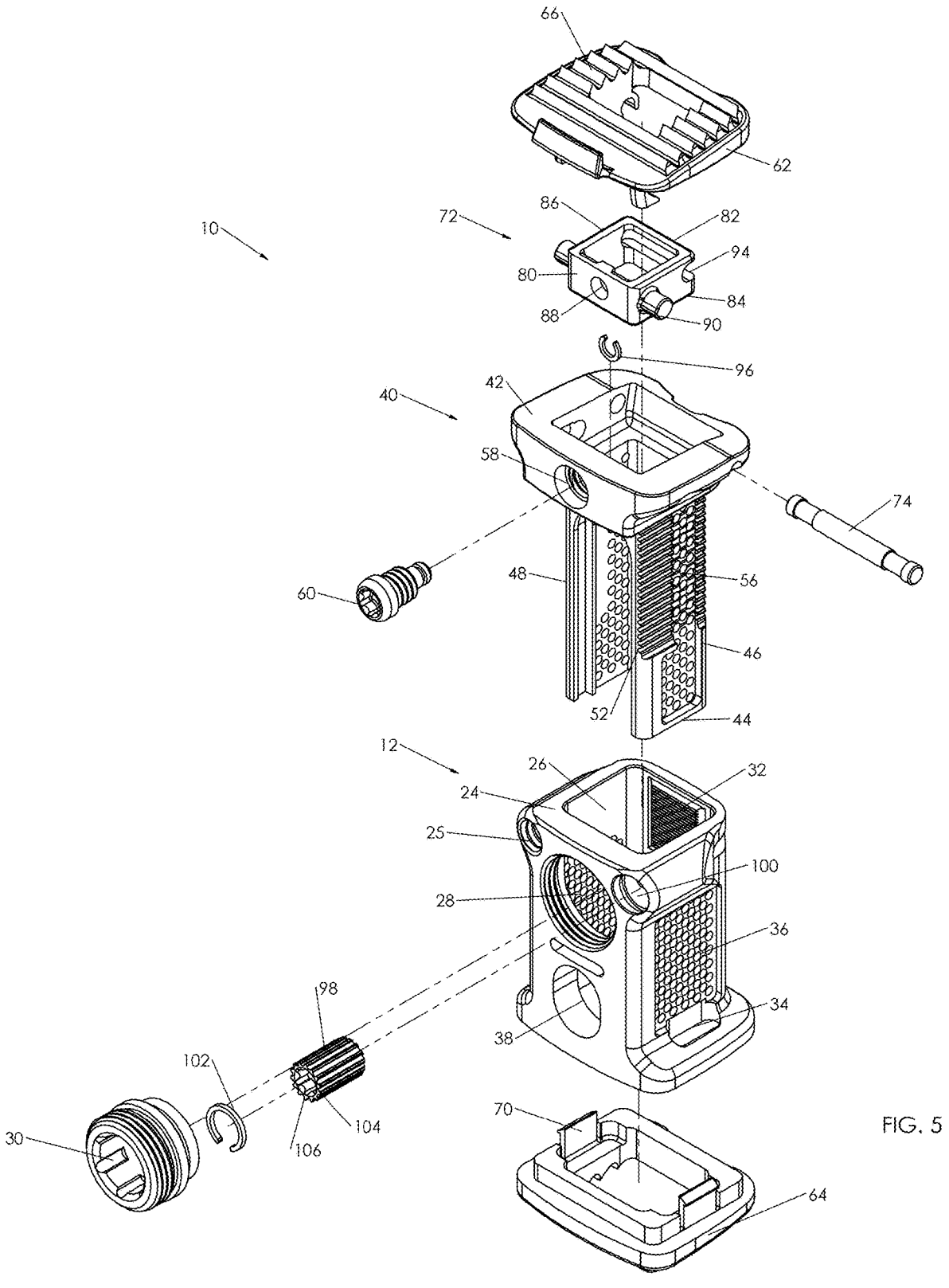
FIG. 5 is a top front exploded view thereof.
Figure 6:
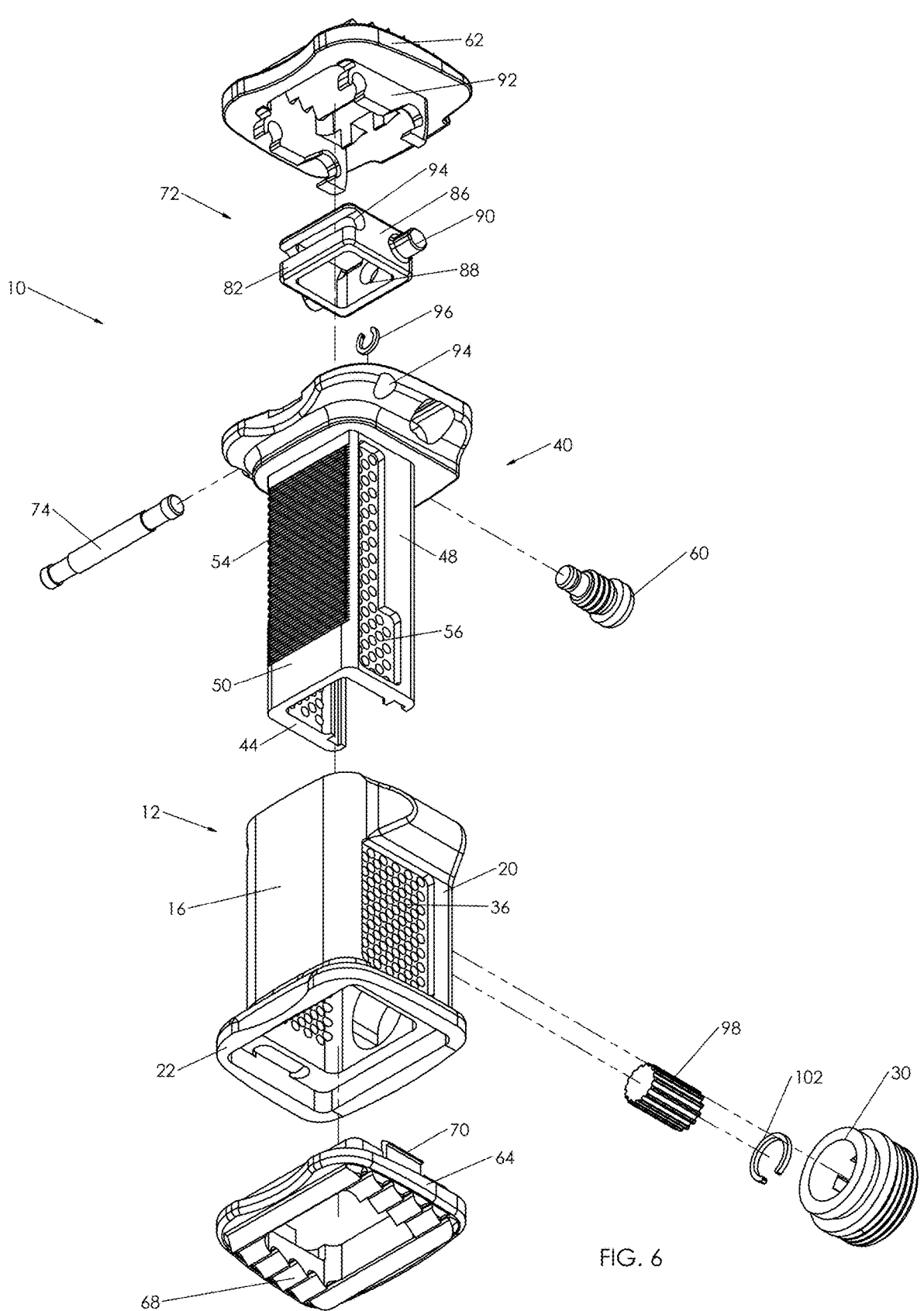
FIG. 6 is a bottom rear exploded view thereof.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

Referring now to the Figures, set forth is a corpectomy device 10 that may be adjusted within the intervertebral cavity in situ. The corpectomy device 10 employs a base member 12 having a front wall 14 spaced apart from a rear wall 16 by a first side wall 18 and a second side wall 20. The first side wall 18 and the second side wall 20 have a common lower edge 22 and upper edge 24 forming a cavity 26 therebetween. The front wall 14 has a centrally disposed aperture 28 having threads for receipt of a lock fastener 30. Further, front wall 14 of the base member 12 includes a tool receptacle 25 where a surgeon can insert a specialized tool to stabilize the corpectomy device 10 during insertion of the device 10 during a patient's surgery.

The rear wall 16 of the base member 12 has an engagement surface 32 formed along an inner surface of the rear wall 16. In a preferred embodiment, the base member 12 also includes at least one slot 34 disposed along either the first side wall 18, the second side wall 20, or both, that is used for the attachment of an endplate 64 underneath the base member 12. Further, the first side wall 18 and the second side wall 20 of the base member 12 may have a plurality of apertures 36 to facilitate bone growth. Bone graft material may be inserted through a graft port 38 to promote bone growth within and surrounding and the corpectomy device 10.

The corpectomy device 10 further employs an expansion member 40 having an upper section 42 and a lower section 44. The lower section 44 is defined by a first side wall 46, a second side wall 48, and a back wall 50 depending from the upper section 42. The first side wall 46 of the lower section 44 has a rack 52 formed along an outer surface. Further, the back wall 50 has a reciprocal engagement surface 54 constructed and arranged to engage with the engagement surface 32 of the base member 12. In a preferred embodiment, the first side wall 46 and the second side wall 48 of the expansion member 40 includes a plurality of apertures 56 to facilitate bone growth. The upper section 42 has a pin member aperture 58 disposed on a front outer surface of the upper section 42 for receipt of a pin member 60. The lower section 44 of the expansion member 40 is slidably insertable in the cavity 26 of the base member 12.

Engagement with the vertebrae occurs at endplates found at either end of the corpectomy device 10. An adjustable upper endplate 62 is secured to the upper section 42 of the expansion member 40. Further, at the lower end of the corpectomy device 10, a lower endplate 64 is coupled to the lower edge 22 of the base member 12. In a preferred embodiment, the upper endplate 62 includes a bone engagement surface 66 and the lower endplate 64 includes a bone engagement surface 68. Each bone engagement surface 66, 68 is designed to interface directly with the bone, providing stability and promoting osseointegration. The bone engagement surfaces 66, 68 are typically textured or coated in order to enhance the grip of the corpectomy device 10, which allows for secure placement and facilitates the growth of new bone tissue around the corpectomy device 10 for long-term stability and support. The pattern, texture, composition, and size of the bone engagement surfaces 66, 68 are not limiting. Further, the lower endplate 64 is attached to the base member 12 via at least one clip 70 that is constructed and arranged to fit into and be secured within the slot 34 of the base member 12.

The adjustable upper endplate 62 has a degree of rotatability allowable by an adjustment member 72. The adjustment member 72 is positioned between the upper endplate 62 and the upper section 42 of the expansion member 40. In a preferred embodiment, the adjustment member 72 is sized to fit within the upper section 42 and defined by a front wall 80, a rear wall 82, and opposing side walls 84, 86. The front wall has a threaded aperture 88 for receipt of the pin member 60. The opposing side walls 84, 86 have tabs 90 extending outwardly therefrom to engage upper endplate clamps 92. Further, the rear wall 82 has a receptacle 94 for engaging a pivot pin 74.

Figure 7A:
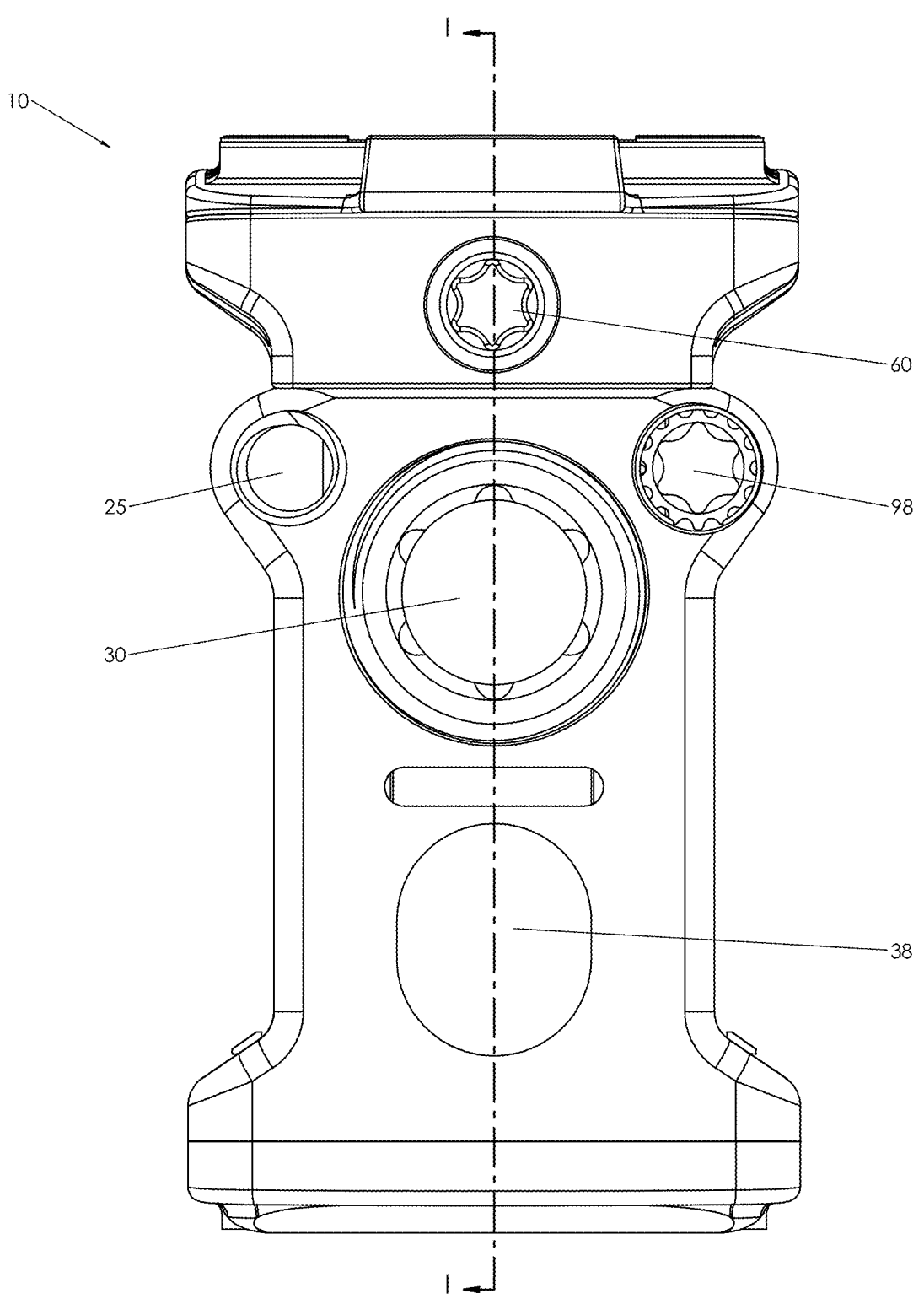
FIG. 7A is a front plane view in a compressed state.
Figure 7B:
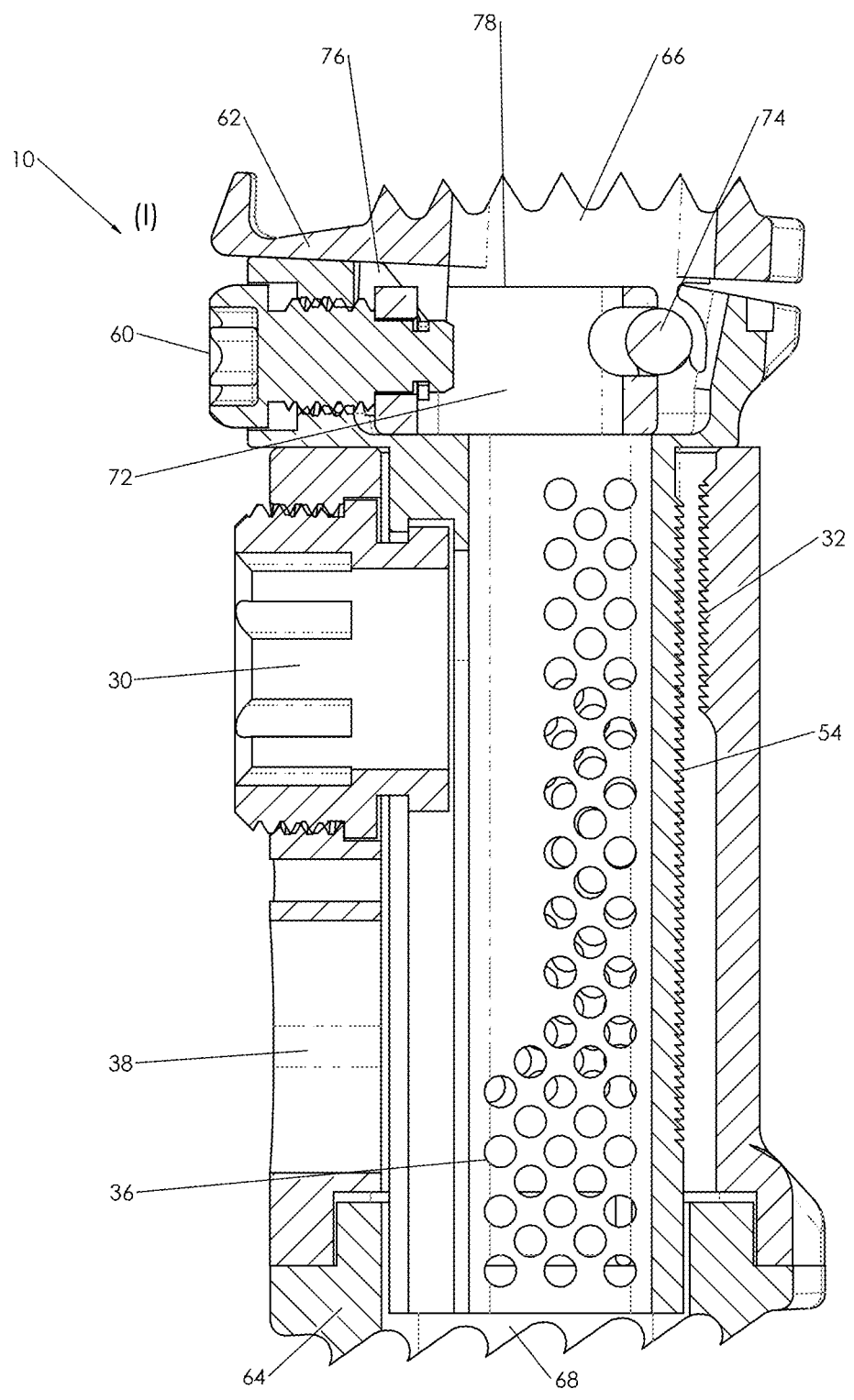
FIG. 7B is a cross sectional view taken along line I-I of FIG. 7A.
Figure 8A:
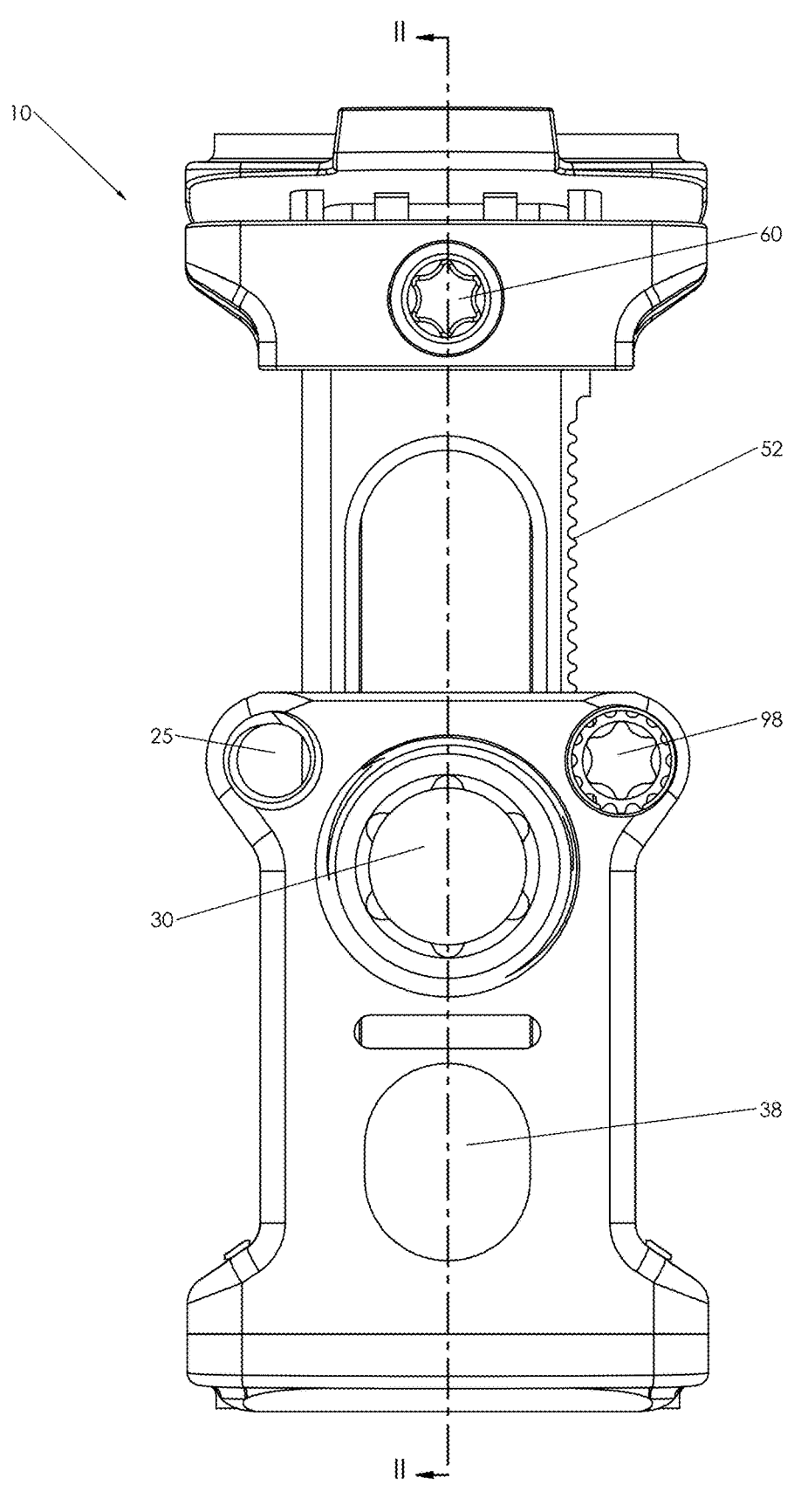
FIG. 8A is a front plane view in a expanded state.
Figure 8B:
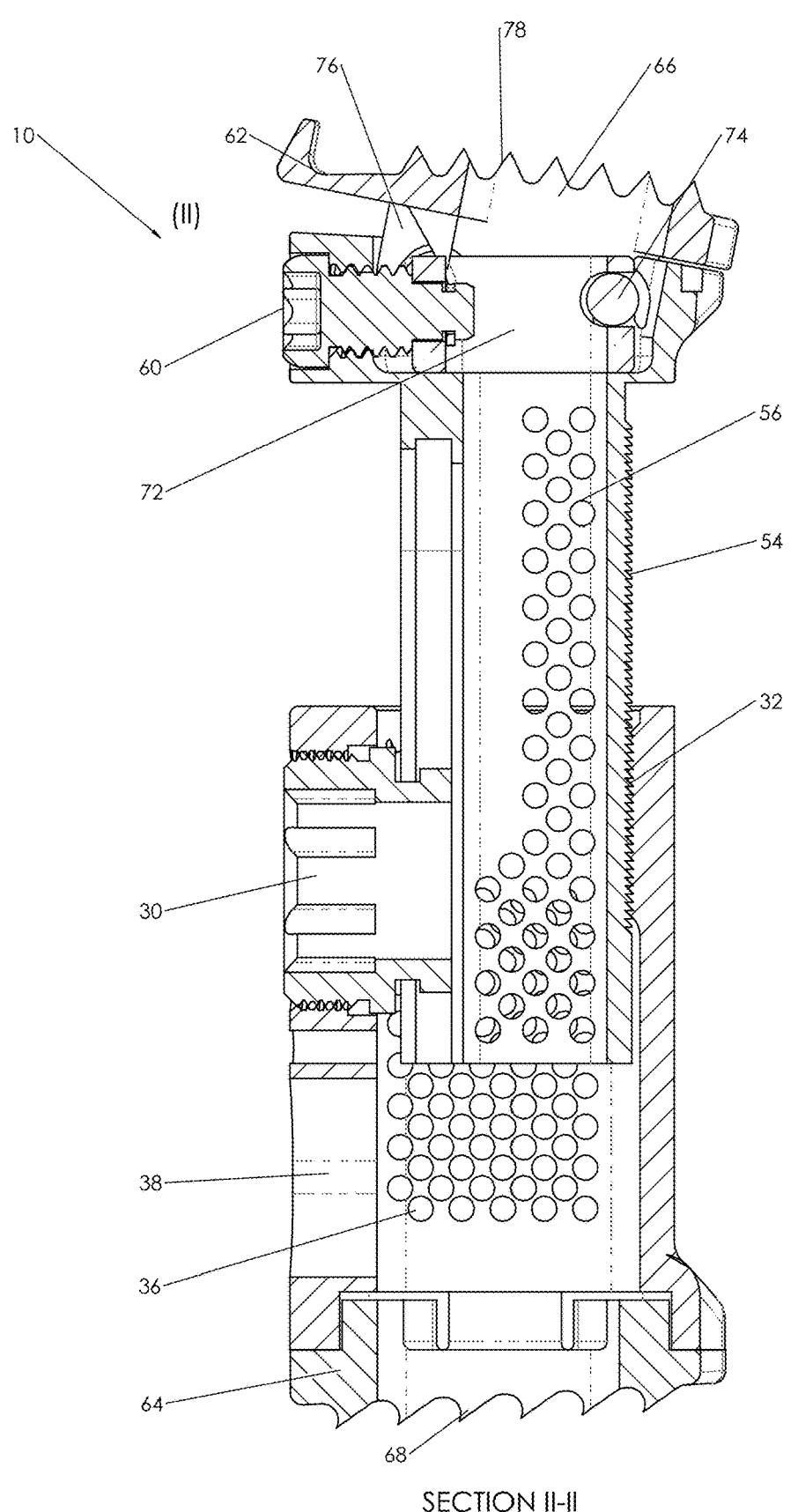
FIG. 8B is a cross sectional view taken along lines II-II of FIG. 8A.
Figure 9:
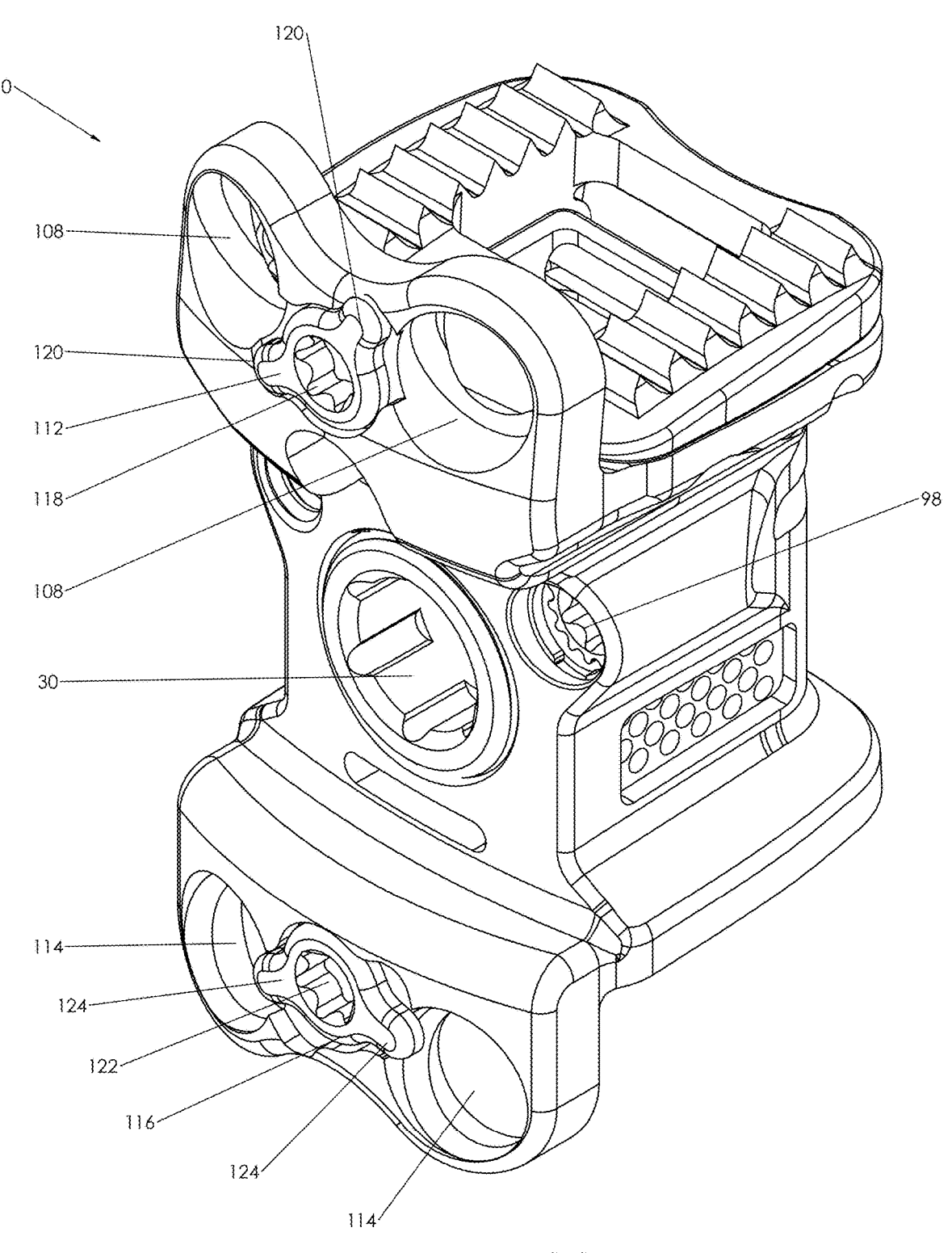
FIG. 9 is a top front perspective view of the corpectomy device in a compressed position with bone screw attachments.
Figure 10:
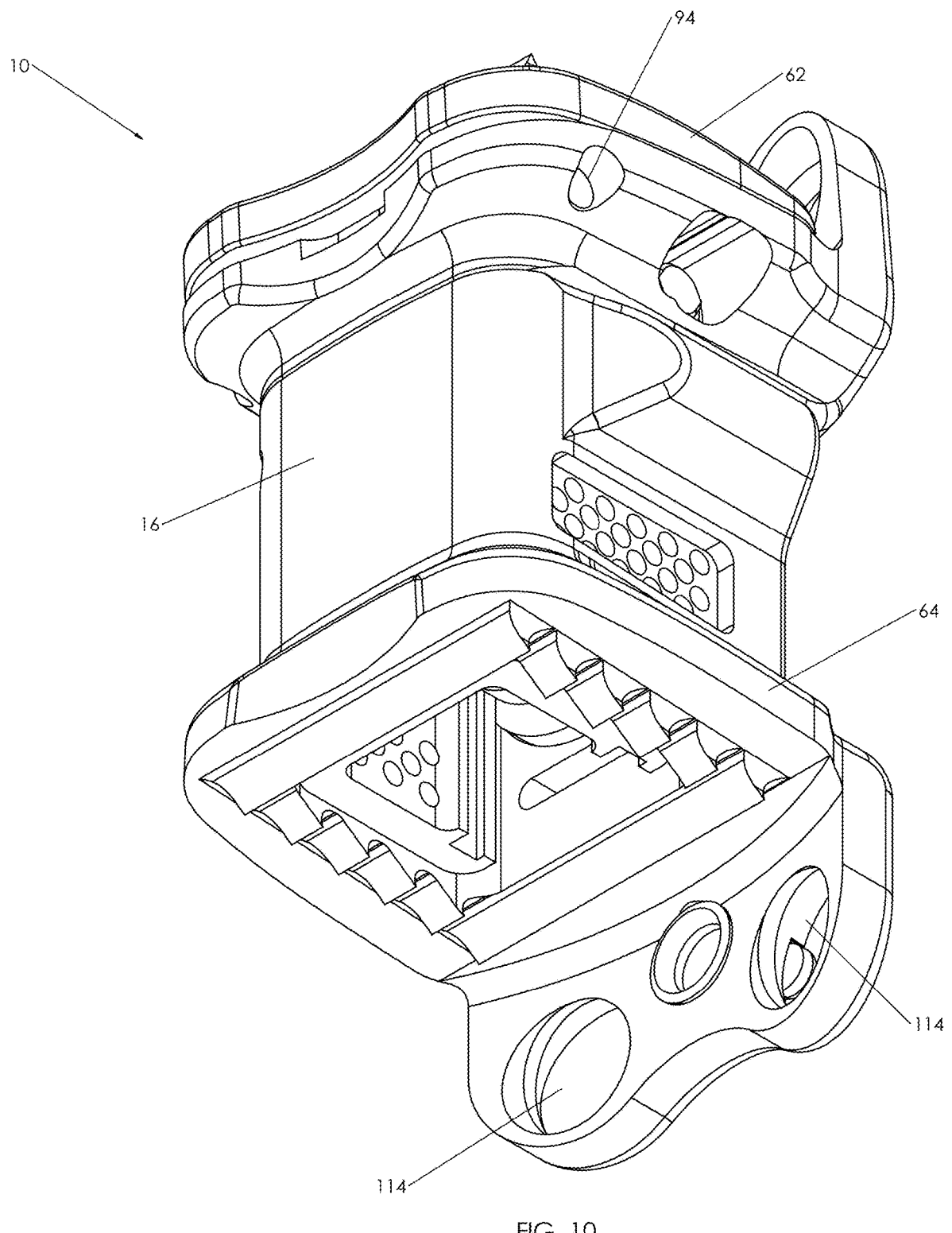
FIG. 10 is a bottom rear perspective view thereof.
Figure 11:
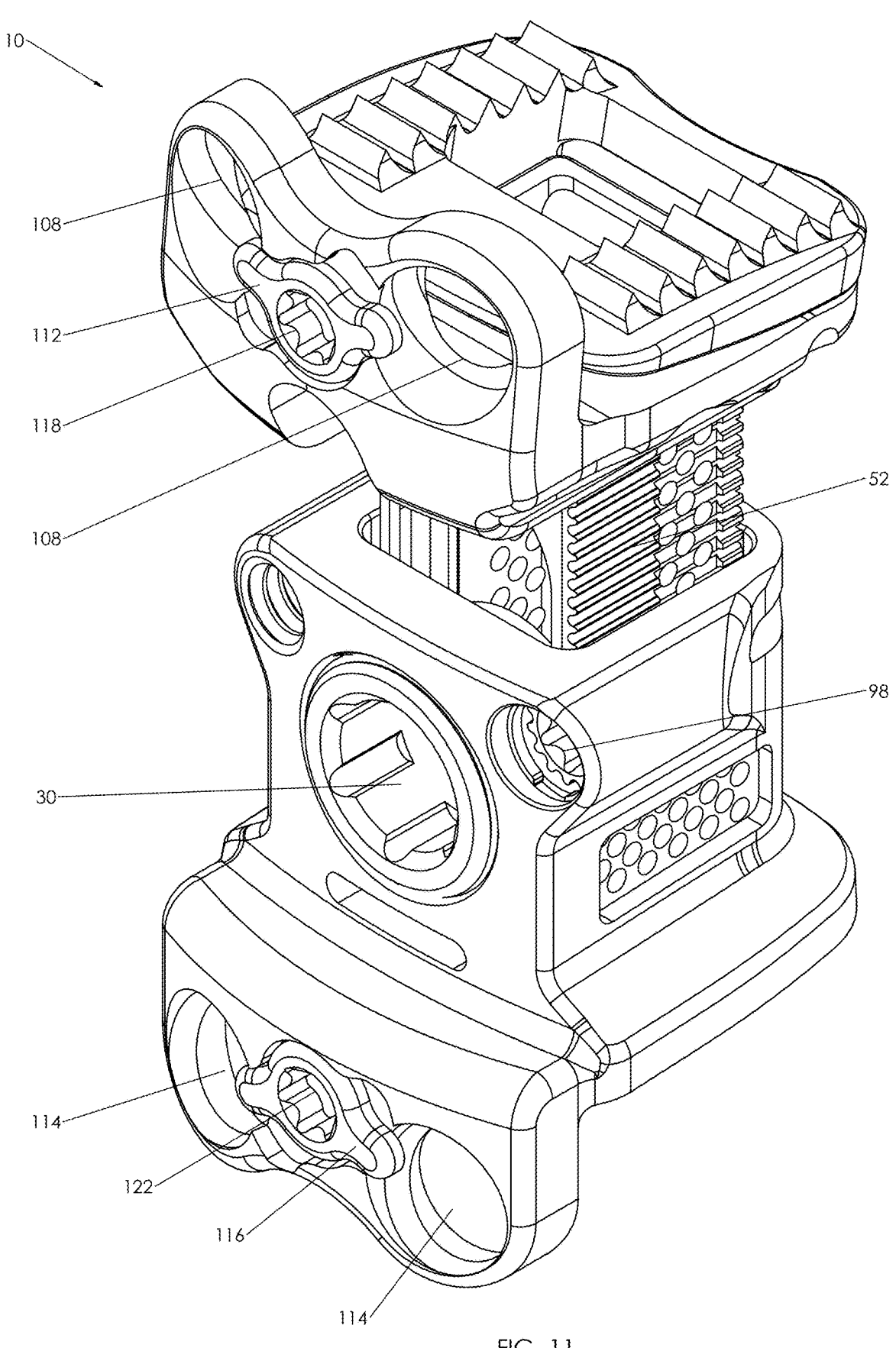
FIG. 11 is a top front perspective view in an expanded position.
Figure 12:
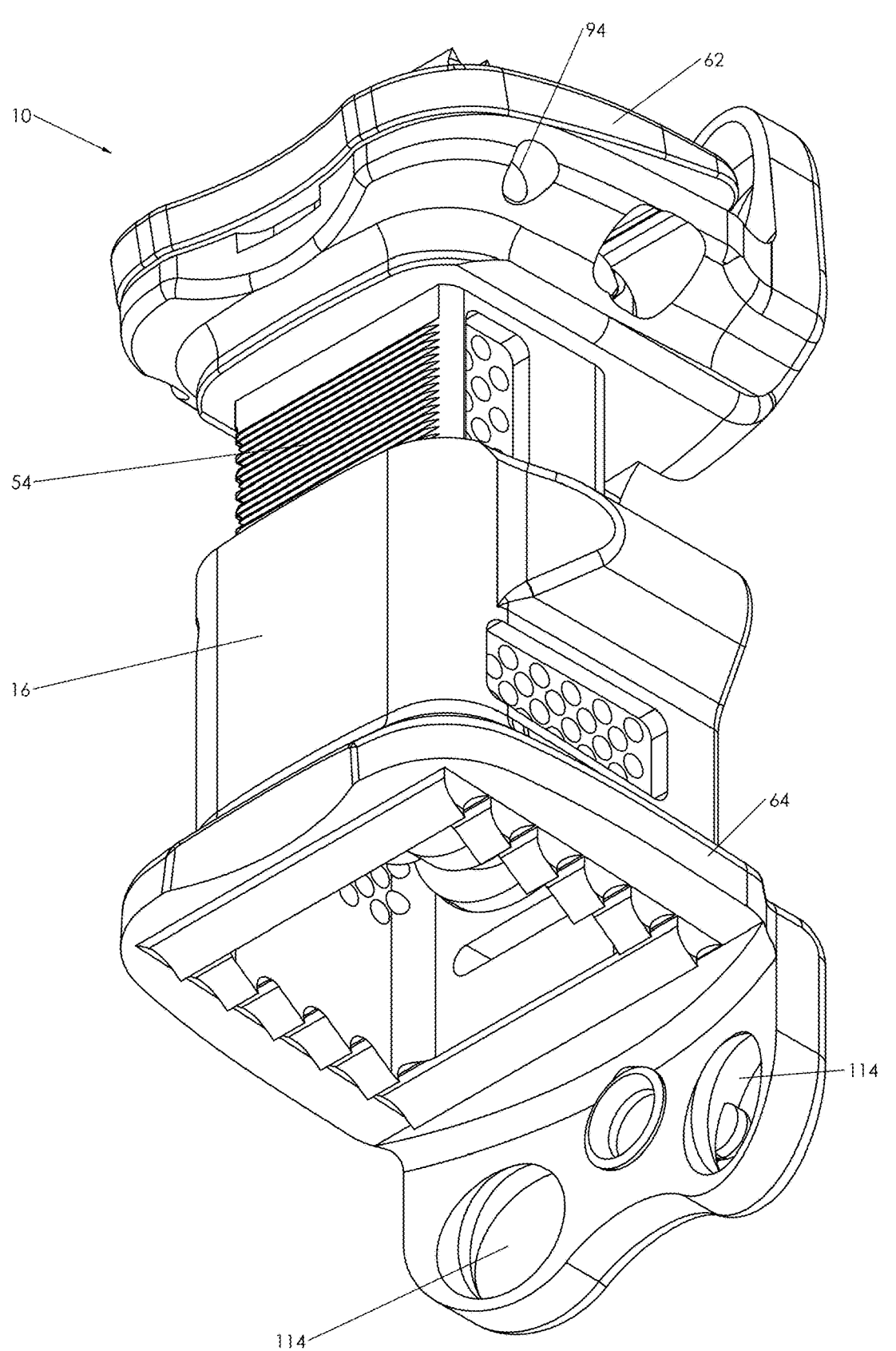
FIG. 12 is a bottom rear perspective view in an expanded position.
Figure 13:
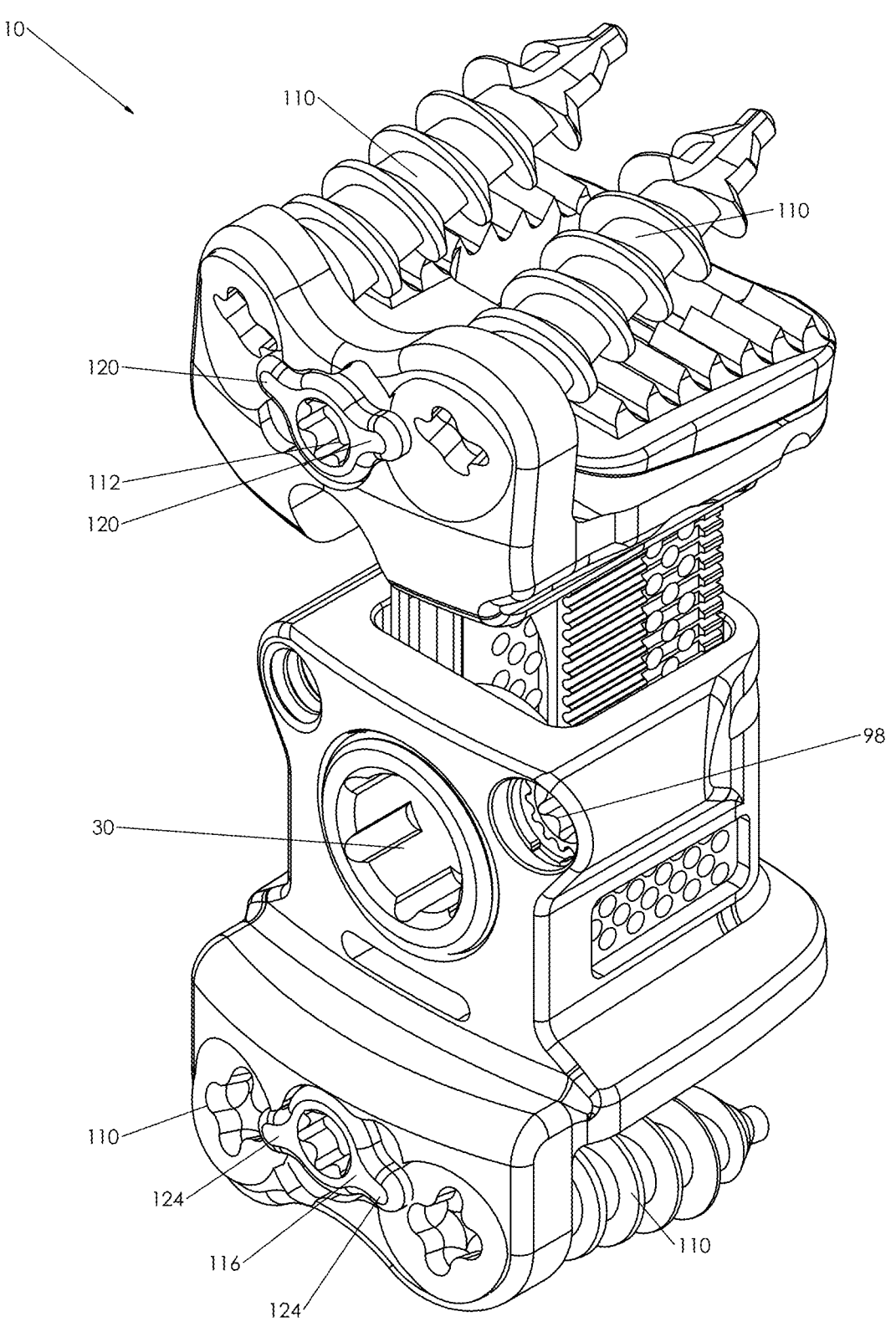
FIG. 13 is a top front perspective view in an expanded position with bone screws.
Figure 14:
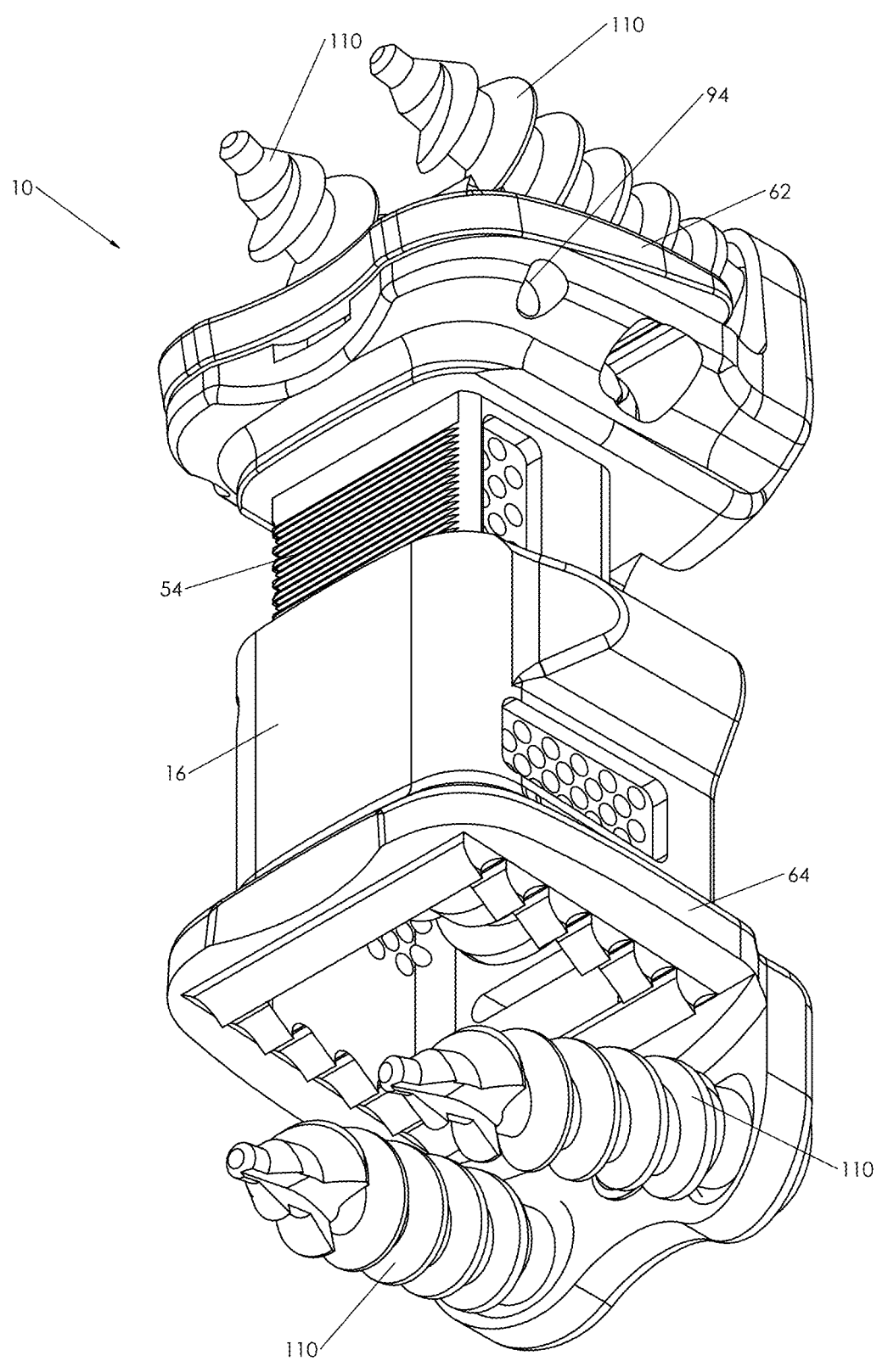
FIG. 14 is a bottom rear perspective view in an expanded position with bone screws.
Figure 15:
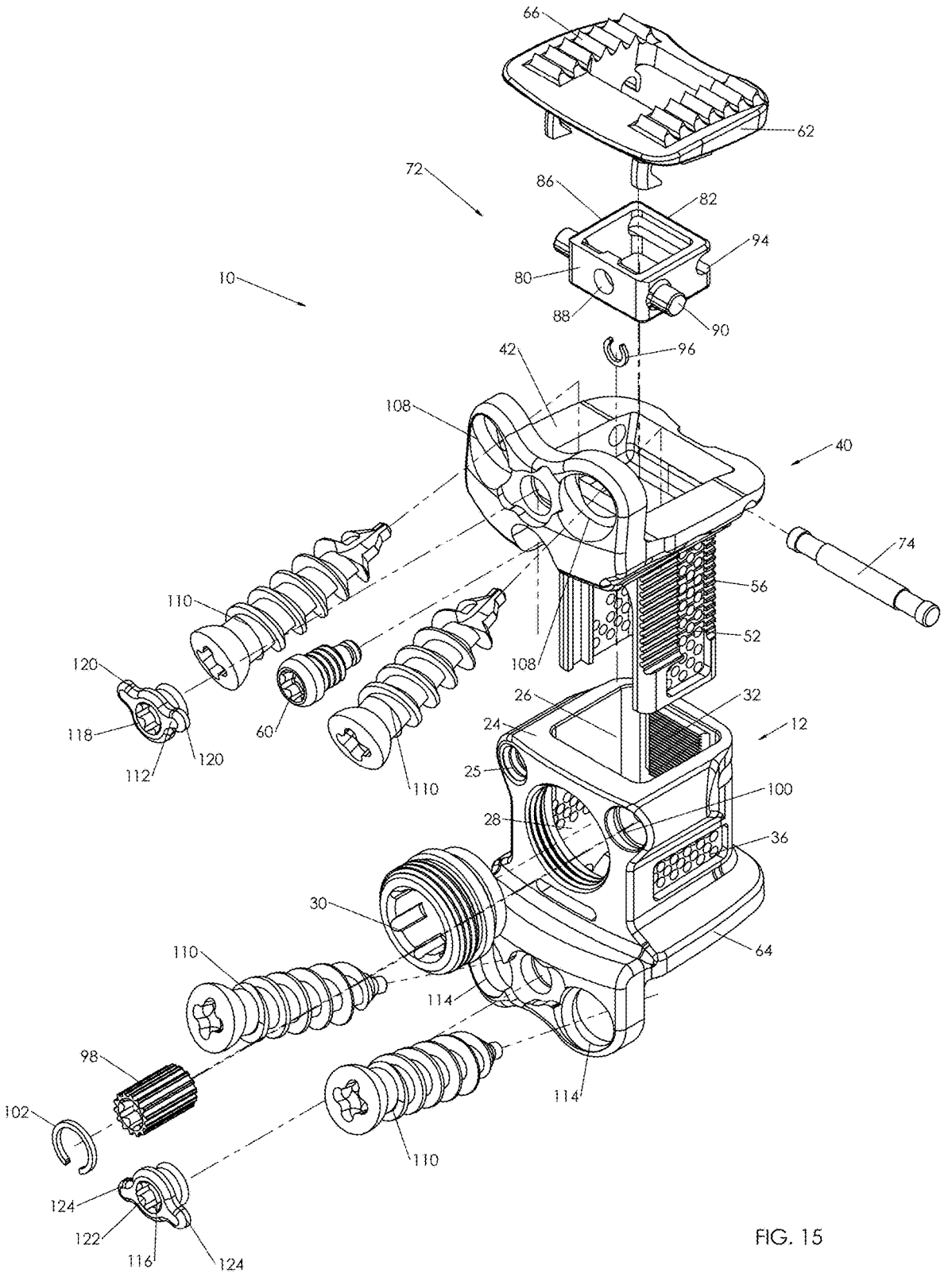
FIG. 15 is a top front exploded view thereof.
Figure 16:
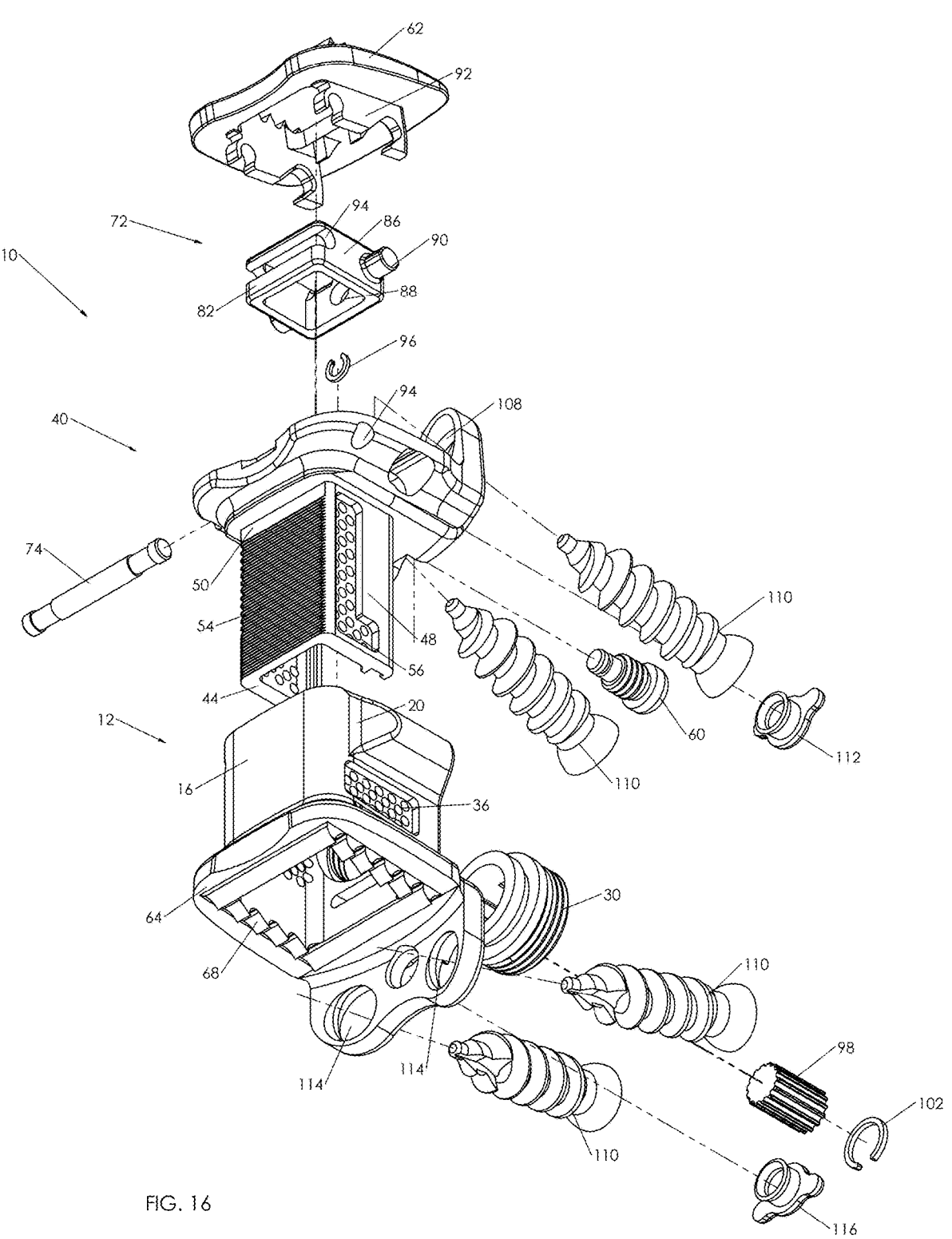
FIG. 16 is a bottom rear exploded view thereof.

The adjustment member 72 is operatively associated with the pivot pin 74 secured to the upper section 42 of the engagement member 40. Likewise, the pin member 60 threadingly engages the adjustment member 72. When the pin member 60 is engaged and threaded inwards, the adjustable upper endplate 62 moves from position (I), as shown in FIG. 7B, that is substantially parallel to the upper surface 42 to an angular position (II), as shown in FIG. 8B, by rotation of the pin member 60.

The pin member 60 itself is rotatably secured to the adjustment member 72 by use of a c-clip 96. As the pin member 60 rotates, this causes ramps 76 on the adjustment member 72 to slide along an upper surface 78 of the adjustment member 72 while the pin member 60 may remain in place with respect to the front outer surface of the upper section 42. The rotation of the adjustable upper endplate 62 allows for precise customization of the corpectomy device 10 with regards to the fit and alignment of a patient's anatomy. The adjustability helps accommodate variations in vertebral endplate geometry, which ensures optimal contact and load distribution of up to 2,000 lbs. of compressive force.

The adjustability of the height of the corpectomy device 10 itself is accomplished by the rotation of a gear member 98. The gear member 98 is rotatably secured to the base member 12 by use of a c-clip 102 within a gear socket 100 located on the front wall 14 and disposed through the side wall 18. The gear member 98 is constructed and arranged to engage the rack 52 of the expansion member 40 wherein rotation of the gear member 98 allows for the raising or lowering of the expansion member 40. The distance between teeth on the rack 52 and the engagement surfaces 32, 54 are sized to allow expansion by predefined increments. In a preferred embodiment, an end wall 104 of the gear member 98 includes a socket 106 for use in rotation wherein rotation of the gear member 98 in one direction expands the distance between the expansion member 40 and the base member 12, and counter rotation of the gear member 98 contracts the distance between the expansion member 40 and the base member 12.

During surgery and after the implantation of the corpectomy device 10, the corpectomy device 10 needs to be locked in place to keep its position. This is achieved via a lock fastener 30. The lock fastener 30 is operatively associated with the aperture 28 formed in the front wall 14 of the base member 12. The lock fastener 30 couples the reciprocal engagement surface 54 of the expansion member 40 to the engagement surface 32 of the back wall 50 of the expansion member 40 against the rear wall 16 of the base member 12. A surgeon will first adjust the height of the expansion member 40 in relation to the base member 12 and then adjust the rotation of upper endplate 62 before locking the corpectomy device 10 in place when the locking fastener 30 couples the expansion member 40 to the base member 12. This process involves using a specialized tool to rotate the socket 106 of the gear member 98 to adjust the height of the expansion member 40 in relation to the base member 12. Next, the surgeon will focus on the pin member 60 engaging the ramps 76 allowing for angular adjustment of the upper endplate 62, and finally the engagement of the lock fastener 30 which arrests movement of the adjustment member 72.

Now referring to FIGS. 9-16, an alternative embodiment of the corpectomy device 10 is shown. In the alternative embodiment, the upper section 42 of the expansion member 40 includes bone screw receptacles 108. The receptacles 108 allow for bone screws 110 to be inserted to engage with an adjacent vertebra for a permanent fixation. To prevent the backing out of the bone screws 110, the bone screw receptacles 108 include a lock mechanism 112 for securing the bone screws 110 in the receptacles 108.

Likewise, the lower edge 22 of the base member 12 includes bone screw receptacles 114. The receptacles 114 allow for bone screws 110 to be inserted to engage with an adjacent vertebra for a permanent fixation. To prevent the backing out of the bone screws 110, the bone screw receptacles 114 include a lock mechanism 116 for securing bone screws 110 in the receptacles 114. The size, shape, and length of the bone screws 110 is not limiting, however, are conforming to fit within the bone screw receptacles 108, 114.

The locking mechanism 112 may include a socket 118 that allows a specialized tool to rotate the locking mechanism 112 to allow the bone screw 110 clearance to enter the bone screw receptacle 108 and may then be rotated so that tabs 120 are seated against the head portion of the bone screw 110, preventing the bone screws 110 from backing out. Similarly, the locking mechanism 116 may include a socket 122 that allows a specialized tool to rotate the locking mechanism 116 to allow the bone screw 110 clearance to enter the bone screw receptacle 114 and may then be rotated so that tabs 124 are seated against the head portion of the bone screw 110, preventing the bone screws 110 from backing out.

The endplates 62, 64 may be connected or permanently attached, such as laser welded, to the corpectomy device. These endplates 62, 64 may be of any desired shape, size or thickness. For example, in one embodiment, the upper endplate 62 is substantially flat with engagement teeth forming a pattern allowing bone securement. Moreover, the shape may or may not correspond to the cross-sectional shape and size (foot-print) of the base. In those instances where the patient presents unusual physiology, such as curvature of the spine (lordosis or kyphosis), additional physiology compensating members may be interposed with the respective endplates. These compensating members allow the corpectomy implant device to take on a more arcuate shape thereby conforming more closely with the existing spinal configuration. The upper 62 and lower endplates 64 are preferably constructed of surfaces for bone engagement including patterns, dimensions, shapes, smooth surfaces, grooved surfaces, rough surfaces, or mobility for engaging a vertebra.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a device that "comprises," "has," "includes" or "contains", possesses those one or more elements, but is not limited to possessing only those one or more elements. Likewise, an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A corpectomy device comprising:

a base member having a front wall spaced apart from a rear wall by first and second side walls, said walls having a common lower edge and upper edge forming a cavity therebetween, said front wall having a centrally disposed aperture, said rear wall of said base member including an engagement surface formed along an inner surface of said rear wall;

an expansion member having an upper section and a lower section, said lower section defined by a first side wall, a second side wall and a back wall depending from said upper section, said first side wall of said lower section having a rack formed along an outer surface, said back wall having a reciprocal engagement surface constructed and arranged to engage said base member engagement surface, said lower section slidably insertable in said cavity of said base member;

an adjustable upper endplate secured to said upper section of said expansion member;

an adjustment member positioned between said upper endplate and said upper section of said expansion member, said adjustment member sized to fit within said upper section and defined by a front wall having a threaded aperture for receipt of a pin member, a rear wall having a receptacle for engaging a pivot pin secured to said upper section, and opposing side walls having tabs extending outwardly therefrom to engage upper endplate clamps, said pin member threadingly engaging said threaded aperture of said front wall of said adjustment member, wherein said adjustable upper endplate is movable from a position substantially parallel to said upper section to an angular position by rotation of said pin member causing ramps on said adjustment member to slide along an upper surface of said adjustment member;

a gear member rotatably secured to said base member, said gear member constructed and arranged to engage said rack of said expansion member wherein rotation of said gear member allows raising or lowering of said expansion member; and a lock fastener operatively associated with said aperture formed in said front wall of said base member, wherein said lock fastener couples said reciprocal engagement surface of said expansion member to said engagement surface of said back wall of said expansion member against said rear wall of said base member;

wherein rotation of said gear member adjusts the height of said expansion member in relation to said base member, and said lock fastener couples said expansion member to said base member in a fixed position.

2. The corpectomy device according to claim 1 wherein said pin member engages said ramps allowing angular adjustment of said upper endplate and engagement of said lock fastener arrests movement of said adjustment member.

3. The corpectomy device according to claim 1 including a lower endplate coupled to said lower edge of said base member, said lower endplate including a bone engagement surface.

4. The corpectomy device according to claim 1 wherein said base member first and second side walls having a plurality of apertures to facilitate bone growth.

5. The corpectomy device according to claim 1 wherein said gear member is rotatably secured to said base member by use of a c-clip.

6. The corpectomy device according to claim 4 wherein an end wall of said gear member includes a socket for use in rotation wherein rotation of said gear member in one direction expands the distance between said expansion member and said base member, and counter rotation of said gear member contracts the distance between said expansion member and said base member.

7. The corpectomy device according to claim 1 wherein said upper endplate includes a bone engagement surface.

8. The corpectomy device according to claim 1 wherein said first and second sidewalls of said expansion member include a plurality of apertures to facilitate bone growth.

9. The corpectomy device according to claim 1 wherein distance between teeth on said rack and said engagement surfaces are sized to allow expansion by predefined increments.

10. The corpectomy device according to claim 1 including a tool receptacle on said front wall of said base member, wherein a surgeon can insert a specialized tool to stabilize said corpectomy device during insertion of said corpectomy device during a patient's surgery.

11. The corpectomy device according to claim 1 wherein said upper section of said expansion member includes bone screw receptacles.

12. The corpectomy device according to claim 11 wherein said bone screw receptacles include a lock mechanism for securing bone screws in said receptacles.

13. The corpectomy device according to claim 1 wherein said lower edge of said base member includes bone screw receptacles.

14. The corpectomy device according to claim 13 wherein said bone screw receptacles include a lock mechanism for securing bone screws in said receptacles.

* * * * *